United States Patent
Jorgenson et al.

(10) Patent No.: US 11,145,409 B2
(45) Date of Patent: Oct. 12, 2021

(54) SINGLE USE AED

(71) Applicant: KONINKLIJKE PHILIPS N.V., Eindhoven (NL)

(72) Inventors: Dawn Blilie Jorgenson, Mercer Island, WA (US); Catherine Anne Thompson, Seattle, WA (US)

(73) Assignee: Koninklijke Philips N.V., Eindhoven (NL)

(*) Notice: Subject to any disclaimer, the term of this patent is extended or adjusted under 35 U.S.C. 154(b) by 157 days.

(21) Appl. No.: 16/049,039

(22) Filed: Jul. 30, 2018

(65) Prior Publication Data

US 2018/0342319 A1    Nov. 29, 2018

Related U.S. Application Data

(63) Continuation of application No. 14/376,312, filed as application No. PCT/IB2013/051135 on Feb. 12, 2013, now Pat. No. 10,055,548.

(Continued)

(51) Int. Cl.
*G16H 40/63* (2018.01)
*A61N 1/39* (2006.01)
(Continued)

(52) U.S. Cl.
CPC ........... *G16H 40/63* (2018.01); *A61N 1/3925* (2013.01); *G09B 23/288* (2013.01); *A61H 31/005* (2013.01); *A61H 31/007* (2013.01); *A61H 2201/501* (2013.01); *A61H 2201/5048* (2013.01); *A61H 2201/5061* (2013.01);
(Continued)

(58) Field of Classification Search
CPC .... G16H 40/63; A61N 1/3925; A61N 1/3968; A61N 1/3993; G09B 23/288; A61H 31/005; A61H 31/007; A61H 2201/501; A61H 2201/5048; A61H 2201/5061; A61H 2201/5084; A61H 2201/5097
See application file for complete search history.

(56) References Cited

U.S. PATENT DOCUMENTS

| 5,591,213 A | 1/1997 | Morgan |
| 5,800,460 A | 9/1998 | Powers et al. |

(Continued)

FOREIGN PATENT DOCUMENTS

| WO | 2008015623 A2 | 2/2008 |
| WO | 2008107841 A1 | 9/2008 |

*Primary Examiner* — Michael Tomaszewski
*Assistant Examiner* — Mohmad Muqueeth

(57) ABSTRACT

An automatic external defibrillator (AED) is described which is leased for an at-risk patient and designed for use in a single cardiac emergency. If the AED is in standby for a year without being deployed, the AED is removed from service and replaced with another AED. The AED requires a rescuer only to deploy the electrodes on the torso of the victim; the AED turns itself on, performs rhythm analysis and delivers a shock if needed automatically. The AED thus requires no user controls. Preferably the AED requires no on-site maintenance, as the AED communicates its readiness for use to a remote monitoring site which responds to any problems detected by self-testing. In addition to its electro-resuscitation function, the AED can be used on the chest of the victim to administer CPR compressions.

5 Claims, 8 Drawing Sheets

Related U.S. Application Data

(60) Provisional application No. 61/604,099, filed on Feb. 28, 2012.

(51) Int. Cl.
    *G09B 23/28*    (2006.01)
    *A61H 31/00*    (2006.01)

(52) U.S. Cl.
    CPC ............... *A61H 2201/5084* (2013.01); *A61H 2201/5097* (2013.01); *A61N 1/3968* (2013.01); *A61N 1/3993* (2013.01)

(56) References Cited

U.S. PATENT DOCUMENTS

| | | |
|---|---|---|
| 6,329,822 B1 | 12/2001 | Powers |
| RE43,050 E | 12/2011 | Lyster et al. |
| 8,086,306 B2 | 12/2011 | Katzman et al. |
| 2003/0114885 A1* | 6/2003 | Nova ................ A61N 1/046 607/2 |
| 2003/0233129 A1* | 12/2003 | Matos ................ G16H 40/63 607/5 |
| 2006/0116723 A1 | 6/2006 | Hansen et al. |
| 2008/0312708 A1 | 12/2008 | Snyder |
| 2010/0023074 A1 | 1/2010 | Powers et al. |
| 2011/0060378 A1 | 3/2011 | Tuysserkani |
| 2011/0257695 A1 | 10/2011 | Jonsen et al. |

\* cited by examiner

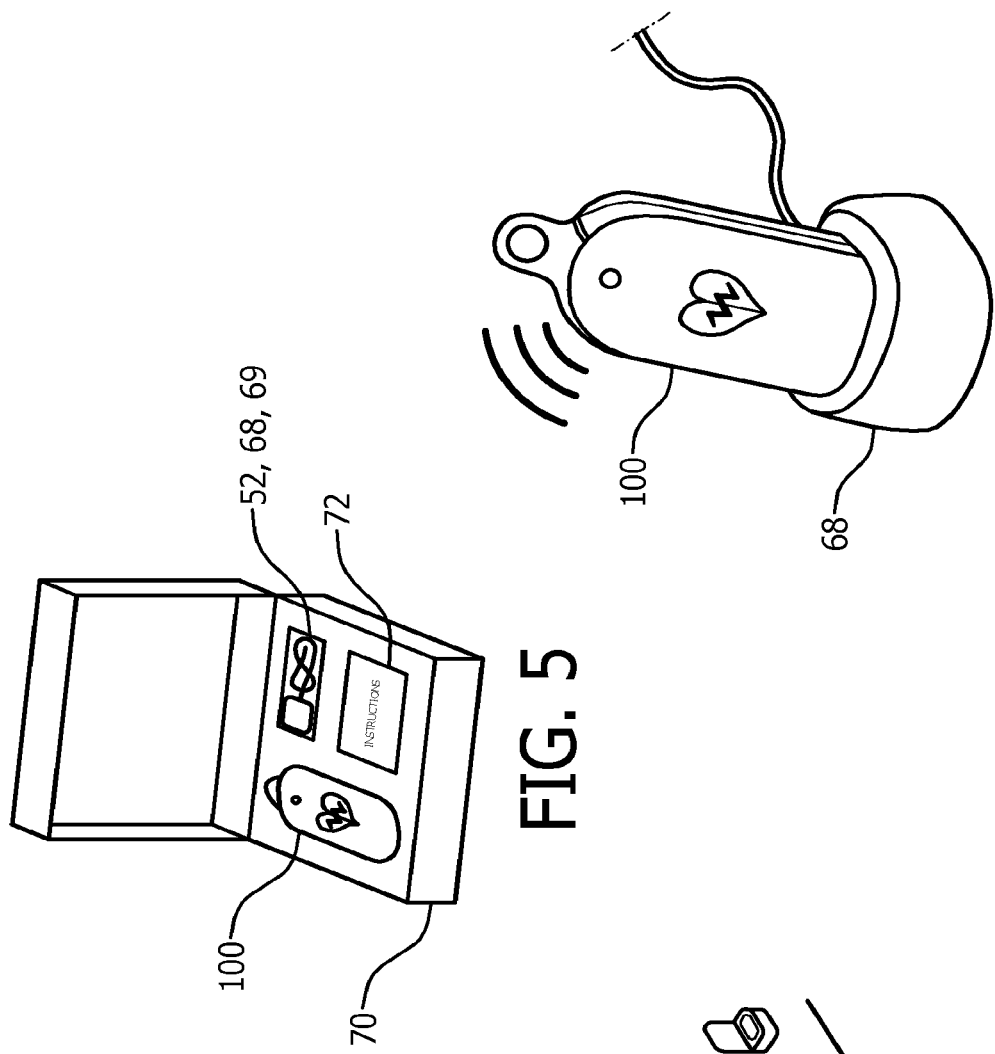
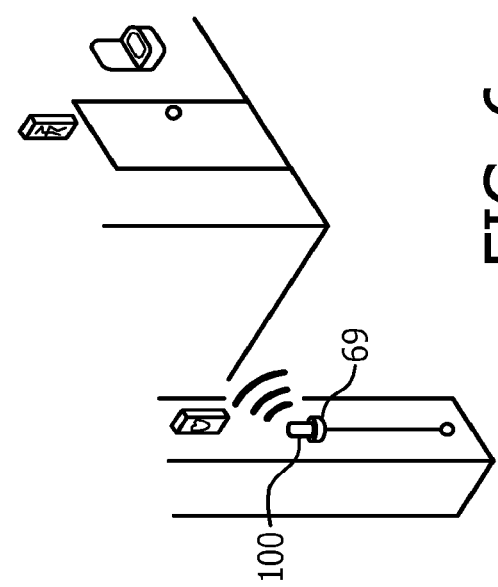

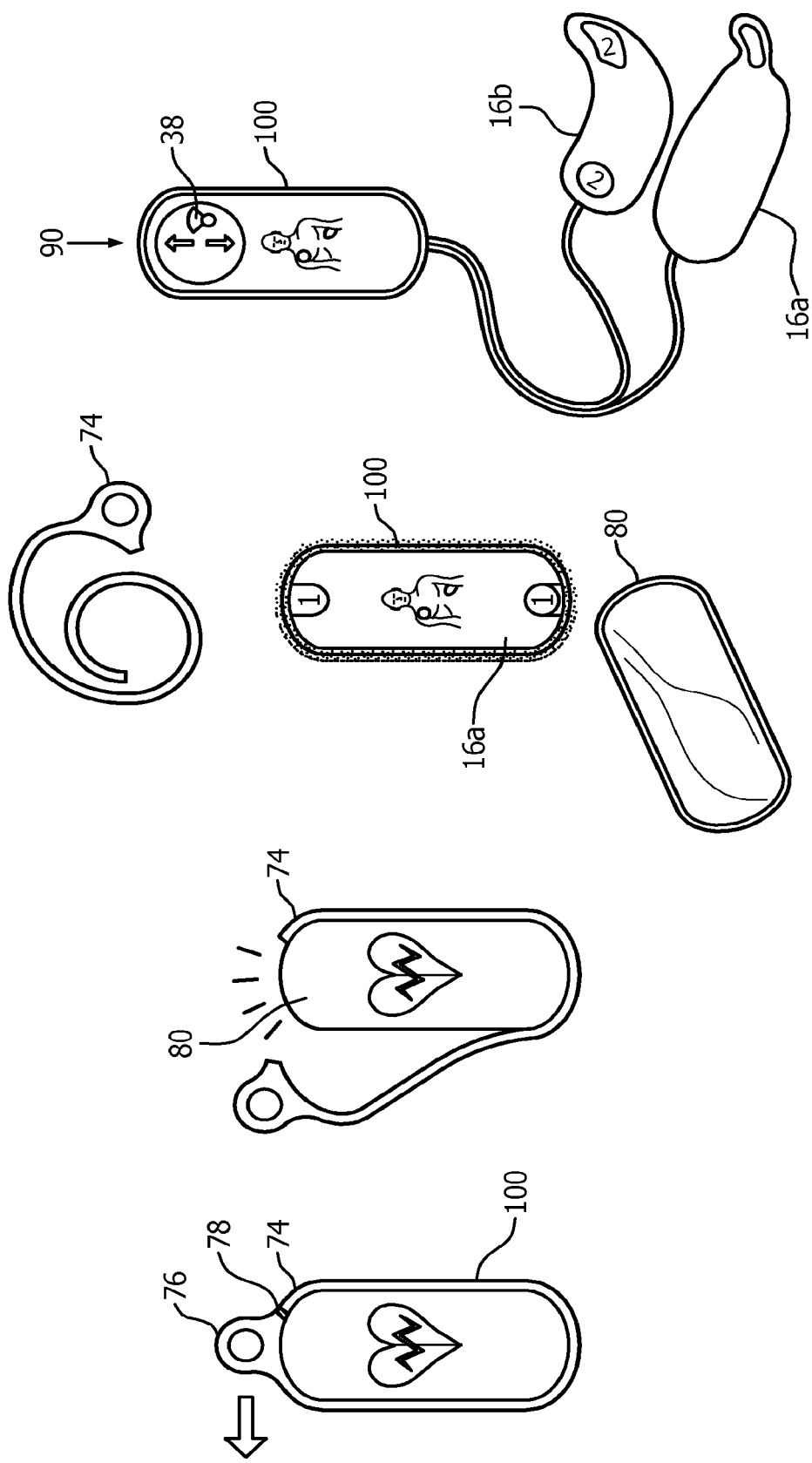

SINGLE USE AED

This application is a continuation application of co-pending U.S. patent application Ser. No. 14/376,312 entitled "SINGLE USE AED" filed on Aug. 1, 2014, which in turn is the U.S. National Phase application under 35 U.S.C. § 371 of International Application No. PCT/IB2013/051135, filed on Feb. 12, 2013, which claims the benefit of U.S. Provisional Patent Application No. 61/604,099, filed on Feb. 28, 2012. These applications are hereby incorporated by reference herein.

This invention relates to automatic external defibrillators (AEDs) and, in particular, to an AED which is designed for use by a layperson responder for a period of time to resuscitate a potential patient and for a single rescue.

AEDs are in widespread use in public facilities like airports, office buildings, schools, and shopping centers and in transportation systems such as commercial airliners. These AEDs are generally prominently located in these facilities so that potential rescuers can quickly and easily locate them. Organizations that own these AEDs usually support them in two ways. One is to check them regularly to make sure they are fully serviceable and ready for immediate deployment. This involves checking the ready light on each AED, the batteries and the electrode pads. These inspections are done regularly such as on a monthly basis. The second support is to put in place a group of first responders, trained and backed by medical personnel, who are available to treat potential patients whenever an emergency arises.

AEDs are also commercially available for use by individuals in private residences, both by prescription and through over-the-counter purchase. Such privately-owned and maintained AEDs do not enjoy the same support structure afforded by large organizations. Since a cardiac arrest victim cannot administer an AED himself, a family member is usually instructed on use of the AED. Subsequent help must be obtained by calling an emergency medical responder as by calling 9-1-1 in the United States. An AED purchaser should set up and initialize the AED when it arrives at home, whereafter the AED will perform some of its own maintenance through onboard self-testing. However, since a home AED is infrequently used, it is often stored out of sight. The family can easily forget to check the ready light illuminated when self-testing finds a problem, and the AED may be stored in a location where audible alerts of problem cannot be heard. The AED may not do self-testing of electrode quality, which means that electrodes must be replaced when they reach their expiration dates. This can often be overlooked in situations where the AED has gone unused for a long period of time.

AEDs are commonly used by emergency medical responders and carried in ambulances, fire trucks, and other emergency vehicles. In these environments the AEDs must be ruggedized for rough handling. The AEDs must also be capable of frequent deployment and use, with batteries and electrode pads designed for quick and easy replacement. In the home environment an AED spends virtually its entire life waiting for a single emergency. Ruggedization and readiness for repeated use is not required for the passive environment of the home.

Accordingly it is desirable to provide AEDs and their support for home use which address these issues and the situation of home storage and use.

In accordance with the principles of the present invention, an AED and support system are described which are targeted for the home or other passive environments. Since the AED will generally be stored for a long period of time in a passive setting, it does not need the ruggedization of an AED designed for mobile first responders. Since a home AED will in all likelihood be used by a family member and not trained medical personnel it does not need the variety of features, settings, and controls of an AED designed for EMS personnel. An AED of the present invention is simple with only a power-on control to power up the AED, start rhythm analysis and deliver a shock automatically without further user intervention. The cost is kept low by leasing the AED to an at-risk patient or rescuer for a predetermined period of time and designing the AED for only a single rescue. If the AED is deployed and used to resuscitate a patient, it is then disposed of or returned to the manufacturer for refurbishment and is replaced by another AED. Periodic maintenance during long-term storage is obviated by returning and replacing the AED periodically such as annually. An annual replacement assures that the battery and electrodes are fully charged and fresh and ready for a rescue during the coming year, and expert maintenance is performed during the refurbishment of the returned AED. The sizeable one-time cost of purchase is avoided by leasing the AED to the consumer, who then only pays for the single year of ownership and service. An AED of the present invention is preferably capable of wireless communication with the manufacturer or AED provider. Should a service problem be detected by the AED during self-testing, a service message is sent to the manufacturer or provider who will then make arrangements with the custodian of the AED for prompt service or replacement of the AED.

In the drawings:

FIG. 5 illustrates a newly arrived AED of the present invention with its packaging, charger and instructions.

FIG. 6 illustrates an AED of the present invention in a wall-mounted charger.

FIG. 7 illustrates an AED of the present invention in a tabletop charger.

FIGS. 10a to 10d are a sequence of illustration showing preparation of an AED of the present invention for a rescue.

Figure 1:
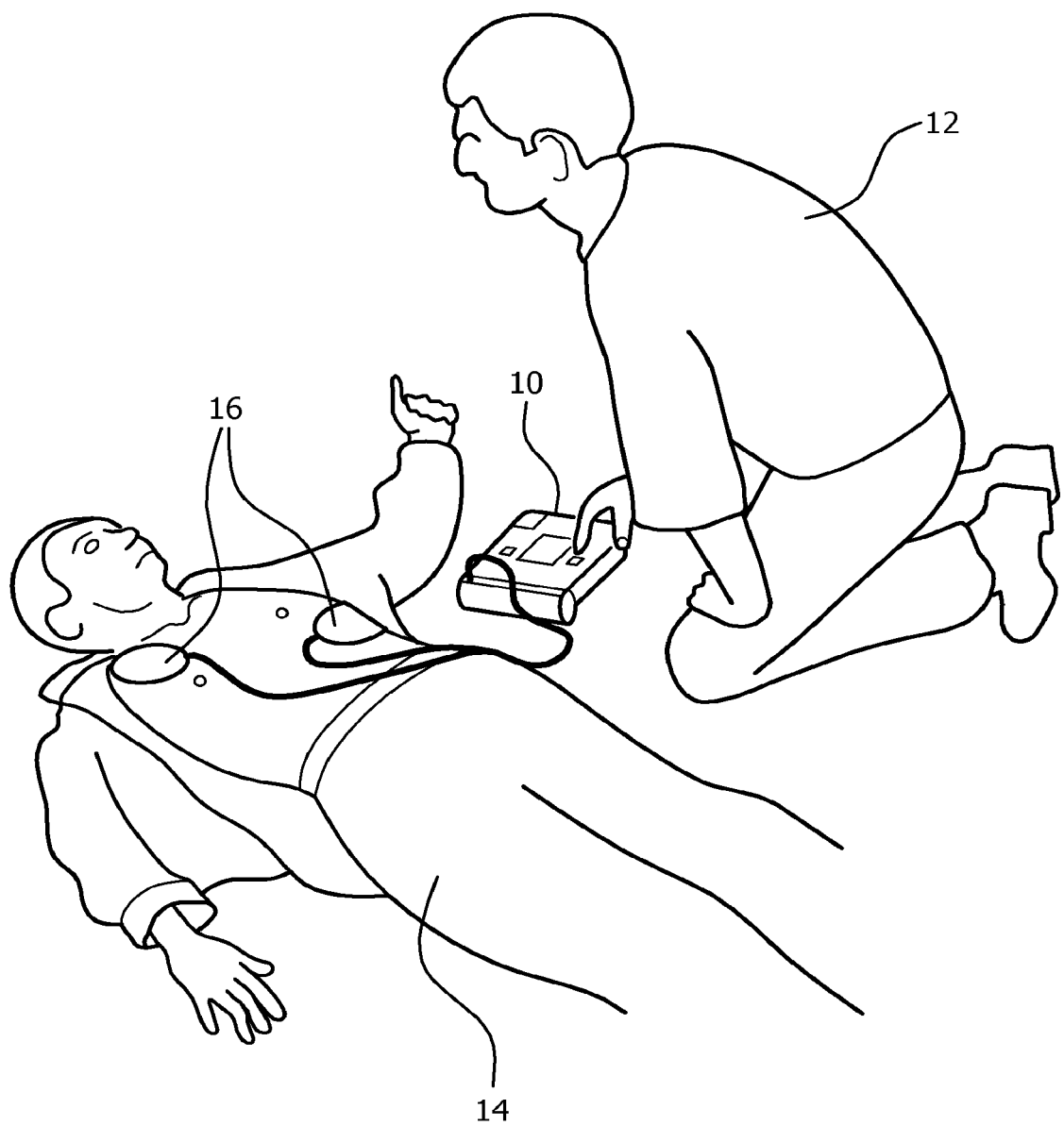
FIG. 1 illustrates a typical rescue of a patient who has suffered cardiac arrest by a rescuer using an AED.

Referring first to FIG. 1, an AED 10 is illustrated being applied by a rescuer 12 to resuscitate a patient 14 suffering from cardiac arrest. In cardiac arrest, the patient is stricken with a life threatening interruption to the normal heart rhythm, typically in the form of VF (ventricular fibrillation) or VT (ventricular tachycardia) that is not accompanied by a palpable pulse (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient 14 will die. Conversely, the quicker defibrillation can be applied after the onset of VF, the better the chances that the patient 14 will survive the cardiac event.

A pair of electrodes 16 are applied across the chest of the patient 14 by the user 12 in order to acquire an ECG signal from the patient's heart. The AED 10 then analyzes the ECG signal for signs of arrhythmia. If VF is detected, the AED 10 signals the user 12 that a shock is advised. After VF or other shockable rhythm has been identified by the AED, the user 12 presses a shock button on the AED 10 to deliver a defibrillation pulse to resuscitate the patient 14.

Figure 2:
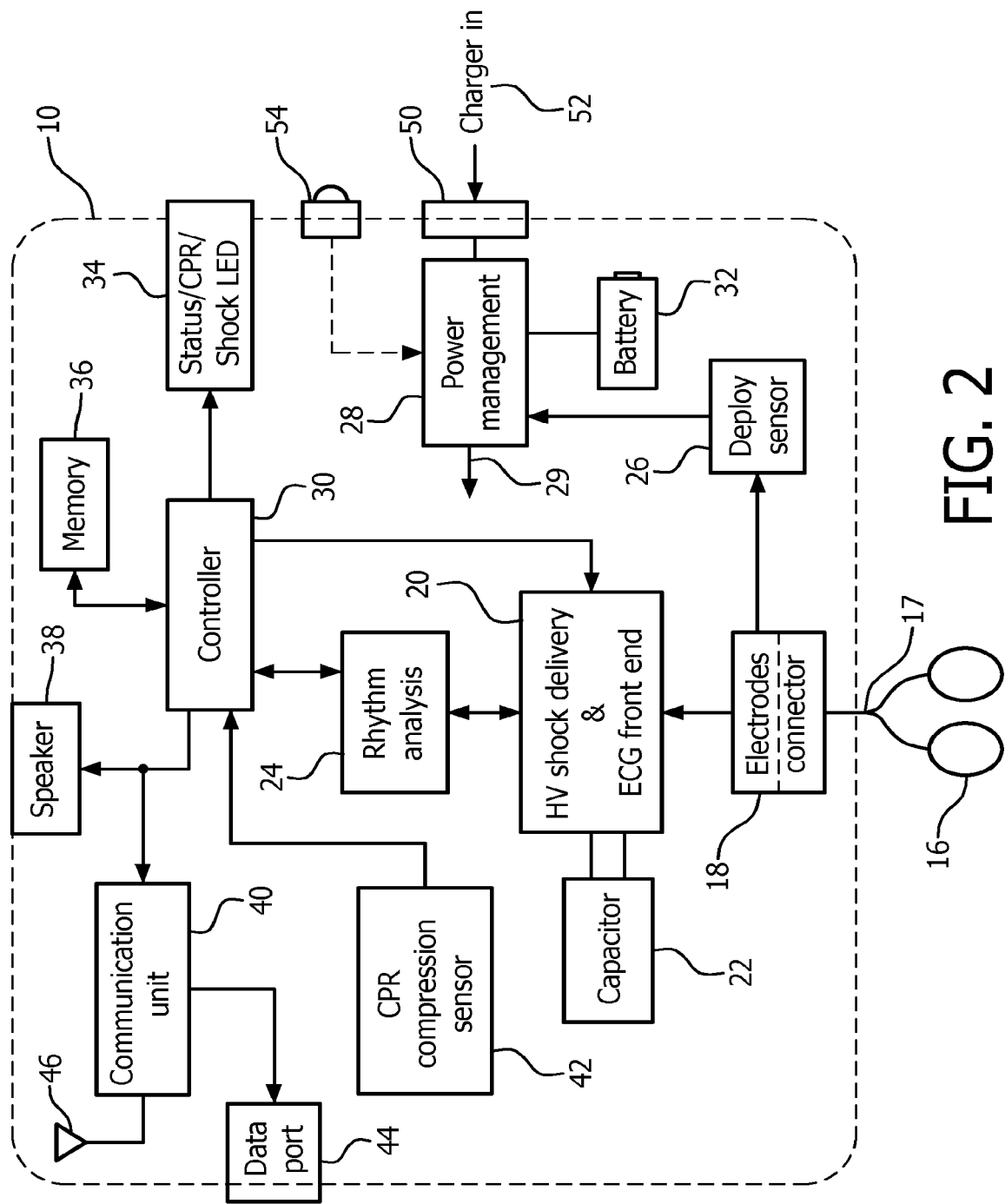
FIG. 2 illustrates in block diagram form an AED constructed in accordance with the principles of the present invention.

Referring now to FIG. 2, an AED constructed in accordance with the principles of the present invention is shown in block diagram form. The dashed outline 10 in FIG. 2 encloses the the components of the AED which are inside the housing 60 of the AED shown in FIG. 3. Electrodes 16 are pre-connected to the AED by lead wires 17. Instead of being plugged into a connector on the exterior of the AED, the electrodes are plugged into an internal connector 18. This can be done for a single use AED of the present invention, as the electrodes are not intended to be replaced by the user after the single use. The internal connector is accessed by factory personnel to remove and replace the electrodes when the AED is returned for refurbishment as discussed below. Alternatively, an external connector can be used so that the electrodes 16 can be unplugged from the AED after a rescue and plugged into the defibrillator of EMS personnel who arrive after the rescue, so that the patient's ECG can continue to be monitored by the EMS defibrillator and additional shocks delivered from that AED should the patient lapse back into ventricular fibrillation after the initial resuscitation. The patient can alternatively continue to be monitored by the single use AED and resuscitated again if necessary by leaving the AED 10 and its electrodes 16 attached to the patient after the initial resuscitation.

The two electrodes 16a, 16b (see FIG. 3) are preferably electrically coupled to each other as by gel-to-gel contact so that they can be self-tested by the AED through the circuit completed by the leads 17 and the electrically coupled electrodes. Such a coupling of electrodes is illustrated in US pat. pub. no. US2011/0257695 (Jonsen et al.) and US RE43,050 (Lyster et al.) As gel electrodes age, the gel can desiccate and its impedance can increase. This poses two potential problems. A dry gel can decrease the ability of the electrodes to stick securely to the thorax of the patients, and a dry gel can have a higher impedance which is in the path of an applied shock, which can impede the effectiveness of the shock and/or cause patient discomfort. To test for gel drying the AED delivers a small signal through the completed electrical circuit of the electrically connected electrodes and by voltage and/or current measurements measures the impedance of the gel. If the gel impedance is above an acceptable level, an alert can be sent as described below. Such impedance measurements are discussed in the aforementioned Lyster et al. reissue patent.

Figure 11:
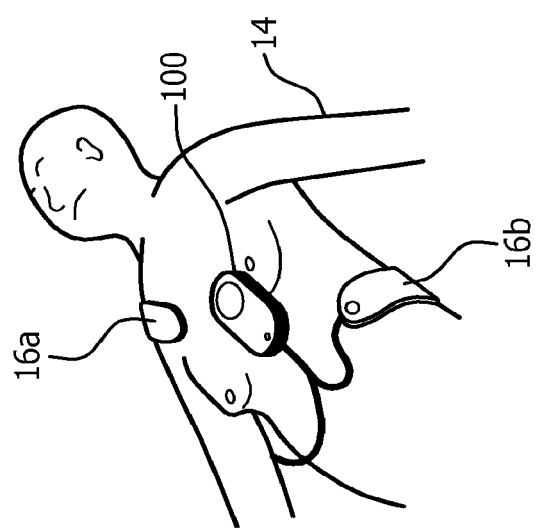
FIG. 11 illustrates the placement of the AED and its electrodes on a victim for a rescue.

While the electrodes are stored they can be attached to opposite sides of a release liner with gel contact provided by an aperture in the release liner as shown in the Lyster et al. reissue patent. Alternatively, the electrodes can be stored in electrical interconnection in an electrode case as shown in FIGS. 5a and 5b of the Jonsen et al. application. Another possibility is to store the electrodes in a separate slide-in electrode case as shown in FIG. 11 of the Jonsen et al. application. Yet another possibility is to integrate an electrode case as shown in FIG. 10 of the Jonsen et al. application as an electrode storage compartment in the AED housing 60. The electrodes are then stored in electrical interconnection inside of and protected by the housing of the AED.

Today's AEDs are stored with a battery that powers the AED periodically for self-test and maintains a sufficient charge to keep the AED in a standby condition for a considerable amount of time while retaining sufficient charge for delivering many shocks for a number of rescues. The AED is not designed to be connected to an external power source, as are hospital defibrillators. In the embodiment of FIG. 2 the AED is designed to be coupled to an external power source during storage. This means that the battery is continually charged to full capacity and ready for use. Since the AED does not have to operate in storage solely on battery power as is the usual case, a smaller battery can be used, reducing the size and weight of the AED. The battery requirements of the described example are further reduced by targeting the AED for single use, a single rescue. Since the AED is to be used for only a single rescue, the battery capacity needs to support the delivery of only a limited number of shocks such as ten shocks. The AED is coupled to an external power source for battery charging, either a.c. or DC, by connecting the AED to a charger 52 during storage or by storing the AED on a docking station 68 or 69 as show in FIGS. 3b and 6, which provides external power. External power can be supplied from an a.c. electrical outlet or from a DC socket as found in a motor vehicle. Charging can be done through direct contact of contacts on the AED 100 with mating contacts of the charger or docking station as shown in FIG. 3a or, since the charger generally does not have to recharge a fully depleted battery but only maintain a charged battery at peak charge, the charging can be done inductively between the charger and the AED as in the case of an electric toothbrush. External power is supplied to a connector or receiver 50 of the AED which is connected to a power management circuit 28. The power management circuit converts the power to a form suitable for use by the AED and distributes power to the electrical components of the AED as indicated by arrow 29. The power management circuit also charges the battery 32 for the AED.

The AED 10 may have an on/off button, a switch 54, or other actuator to turn the AED on when it is needed for a rescue. Preferably, however, the AED turns itself on when it is deployed for use, eliminating the need for an on/off button. A rescuer unfamiliar with the AED thus does not have to be concerned about how to turn on the AED as the AED will power itself on. One way for the AED to turn itself on is with a deployment sensor in the integrated electrode storage compartment of the AED as described above. When the electrodes are removed from their storage compartment, their removal is sensed as by an optical or spring-loaded switch and a deployment sensor 26 responds by turning on the AED with an output coupled to the power management circuit 28. Another way to turn on the AED is to sense the removal of external power when the AED is unplugged from the charger 52 for transport to the victim and use this change of condition to power on the AED. Yet another way, when a docking station 68, 69 is used, is to optically, electronically, or physically sense the removal of the AED from the docking station and use this sensing to have the power management circuit power up the AED. Yet another approach is to sense handling of the electrodes such as when the electrodes are peeled away from their release liner as described in US pat. pub. no. US2006/0116723 (Hansen et al.) This handling of the electrodes is sensed by the deployment sensor 26 and used to alert the power management circuit 28 and turn on the AED.

The electrode connector 18 is coupled to a high voltage shock delivery and ECG front end circuit 20. This circuit receives patient ECG signals from the electrodes, digitizes the signals, and presents them to a rhythm analysis processor 24 in a form suitable for analysis of the presence of a shockable heart rhythm. When a shockable rhythm is identified by the rhythm analysis processor, energy from the battery 32 is used to charge capacitor 22 and the circuit 20 delivers a shock to the patient through the electrodes 16 using the energy stored on the capacitor, preferably in the form of a biphasic shock waveform. One or more shocks may be delivered by the circuitry 20 in accordance with a shock delivery protocol directed and controlled by a controller 30, which controls shock delivery and other functions of the AED. The controller executes software for the AED which is stored on a memory 36. The memory 36 can also be used to store data produced during a rescue, referred to as "event data," including ECG signal information and shock delivery information and timing. The controller 30 also produces voice prompts to direct a rescuer which are audibly reproduced by a speaker 38. During cardiopulmonary resuscitation (CPR), the controller causes the speaker to produce metronome beeps at the rate at which chest compressions are to be applied to the victim, and also verbal instructions to guide the administration of chest compressions such as "press deeper" or "press faster" to help the rescuer perform effective CPR.

The controller 30 controls the state of a status LED 34, the single display item on the AED of FIG. 2. When the AED is in storage in standby mode and electrically connected to its charger or docking station, the controller causes the LED 34 to illuminate a steady green color. The steady green light indicates that the AED is being charged and is fully operational and ready for use. When the AED is removed from its charger or docking station and is fully operational and ready for use, the steady green light changes to a blinking green light. The controller executes self-test routines periodically to test various functions and capabilities of the AED, such as the charge level of the battery 32, the quality of the electrode gel, the accuracy of the rhythm analysis processor in processing test ECG data, the ability of the high voltage circuitry to charge the capacitor 32, and the like. Typical self-tests for an AED are described in U.S. Pat. No. 5,591,213 (Morgan), U.S. Pat. No. 5,800,460 (Powers et al.), and U.S. Pat. No. 6,329,822 (Powers). Some of these tests are performed fairly frequently, e.g., daily, such as checking the battery charge. Others are performed less frequently such as weekly or monthly, such as testing the rhythm analysis circuit 24 or the charging of the capacitor 32. As long as all the self-test results are positive, the LED 34 continues to illuminate a green color. If a self-test reveals a problem with a non-critical function or component that would not render the AED unsafe or inoperable, such as a slightly longer time needed to charge the capacitor 22 to a level necessary for shock delivery, the controller causes the LED to illuminate in a yellow color. If a self-test reveals a critical failure or unsafe condition, the LED is caused to illuminate a steady red color. Any failure of a self-test in the exemplary AED of FIG. 2 also causes a message to be sent to a maintenance person or facility to immediately address the problem. The controller forwards the appropriate message about the problem to a communication unit 40. A suitable communication unit for an AED is described in international patent publication WO 2008/107841 (Morgan). The communication unit can communicate by a wire line as by connection to a telephone line in the docking station. Alternatively the communication unit can connect wirelessly over a cellphone network or a wireless data link (e.g., WiFi). Another alternative is to locate the communication unit in the docking station where it is in communication with the AED and is powered by the external power source and not the AED battery. Yet another possibility is to partition the communication unit, with a short-range transceiver in the AED and a longer range transceiver in the docking station. A Bluetooth transceiver can be located in the AED, with a telephone or cellphone transceiver in the docking station communicating with both the AED Bluetooth transceiver and a remote location via wired or wireless telephony. A data port 44 may be coupled to the communication unit 40 to communicate digitally by wire with the maintenance person or facility. Depending on the message content, the maintenance person or facility can respond in several ways. A message can be sent to the communication unit 40, instructing the AED to render itself inoperable. A call can be made to or a message sent to the custodian of the AED, instructing the custodian to send the AED back for replacement or notifying the custodian that a new AED will be delivered soon to replace a faulty AED. The message may also cause the AED to emit an audible tone or message that will attract the attention of the custodian to the problem, as described in US Pat. pub. no. US2010/0023074 (Powers et al.) Preferably the faulty AED is swapped out for a different, fully functioning AED and the faulty AED returned or taken back for diagnosis and repair.

The LED 34 is also used during the administration of CPR chest compressions. During the CPR period the LED blinks at the same rate as the beeping metronome sound, giving a visual cue to the rescuer of the rate at which chest compressions should be applied. During preparation for and execution of shock delivery the LED 34 blinks rapidly in red and an accompanying audible alert is issued from the speaker 38, telling the rescuer not to touch the patient while the heart rhythm is being analyzed and a shock may be delivered. After a few seconds of this pre-shock alert, a shock is automatically delivered by the AED when needed. There is no need for the rescuer to press a shock delivery button as the AED has no buttons.

The AED of FIG. 2 includes a CPR compression sensor 42 so that the AED can be used in the administration of CPR chest compressions. This sensor can be a force or acceleration sensor that senses the pressure or depth of chest compressions and this information is coupled to the controller 30. The controller analyzes the information which identifies the rate or frequency of chest compressions and the depth of compression of the victim's chest. The controller uses this information to issue appropriate prompting instructions through the speaker 38, such as "press faster" or "press deeper." Another form of sensor which can be used is one or more snapdomes which produce a distinctive clicking sound when a certain level of pressure is applied and/or released. The snapdome can be located on the top or bottom of the AED housing 60 where it is in line with applied CPR compressions. When a chest compression is applied with a desired level of force, the snapdome clicks when the desired force level is attained. The snapdome will click again when the force is appropriately release at the end of the chest compression. An alternative approach is to use an electronically controlled device which produces a tactile sensation through the housing 60 that can be felt by the rescuer when compressions are applied and released as described in international patent pub. no. WO 2008/015623 (Bishay et al.)

Figure 3:
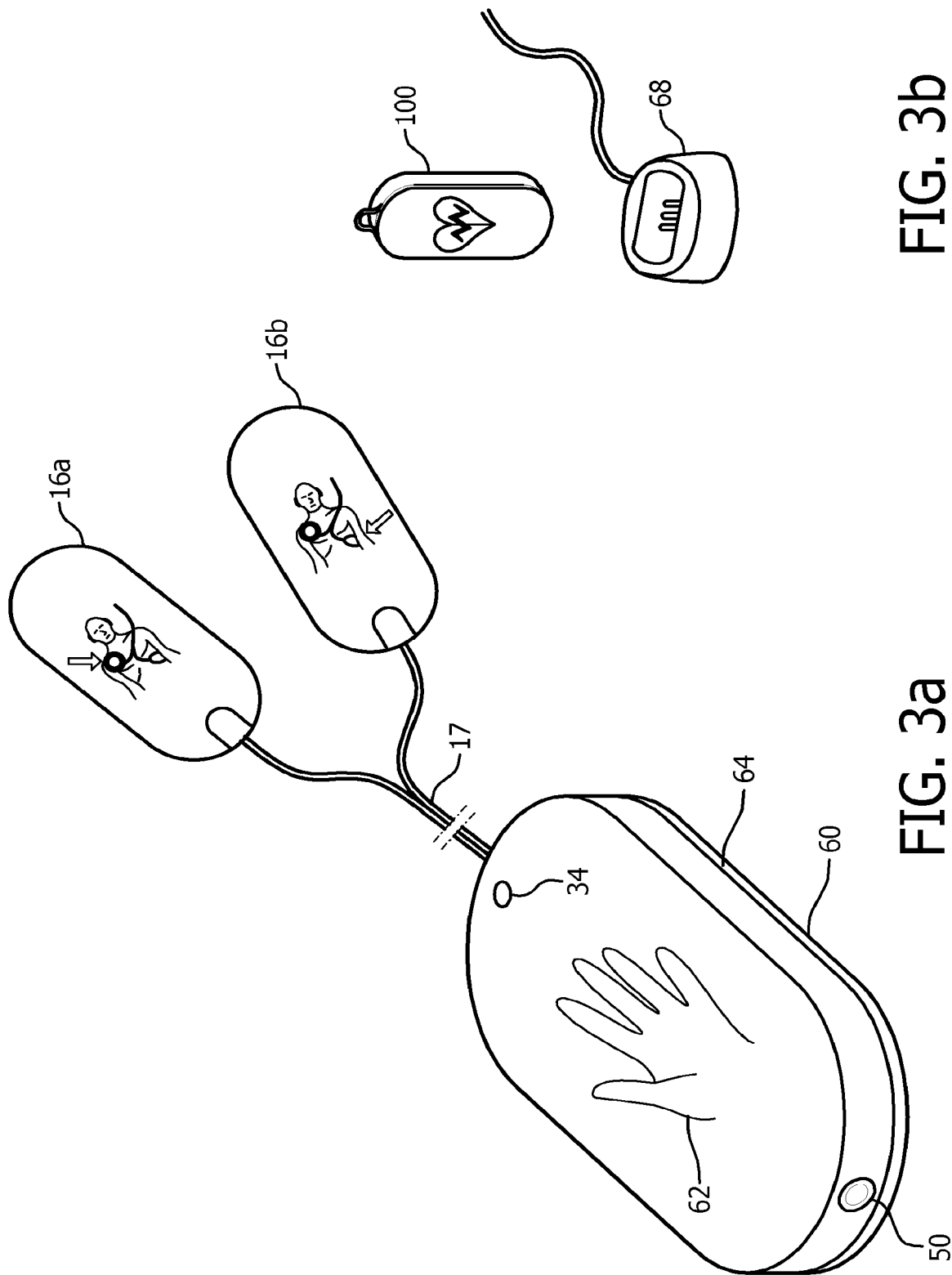
FIG. 3a is a perspective view of an AED of the present invention.
FIG. 3b illustrates an AED of the present invention and its charger/holder.

The AED of FIG. 2 can be housed in a relatively small case or housing 60 as shown in FIG. 3. The exemplary housing in FIG. 3 is about 15 cm. high by 10 cm. wide by 2.5 cm deep. The capacitor 22 inside the housing has dimensions of approximately 2.5 by 4.5 by 1.2 cm. The battery is similarly sized. The complete AED weighs less than one kilogram. The leads 17 to the electrodes 16a, 16b are seen to extend from one end of the housing and the charging connector 50 is visible at the other end of the housing. Alternatively the leads 17 can exit the housing in the directions of electrode placement, one toward the upper right torso and the other toward the lower left rib cage. The LED 34 is on the top of the housing where it is visible during the administration of CPR. As mentioned above, in a preferred embodiment the AED is also intended to be used in the application of chest compressions, which are applied as indicated by the hand graphic 62 on the top of the AED. To avoid injuring the chest of the patient with hard edges, the edges on the bottom of the housing 60 are rounded or formed of or covered with a soft rubber-like material 64. The rubber-like material also helps prevent the AED from slipping on the chest as compressions are applied. As FIG. 3 illustrates, an AED of the present invention is intended to be very small and light with a clean design. In the illustrated embodiment there are no buttons, switches or controls to confuse and confound a rescuer. All that a layperson rescuer has to do is deploy and attach the electrodes as shown by the electrode graphics and stand back from the patient. The AED automatically analyzes the cardiac rhythm and automatically delivers a shock if one is needed.

When the AED of FIGS. 2 and 3 is put to use it is detached from the charger or removed from its docking station and taken to the victim. The electrodes are deployed and attached to the chest of the victim as illustrated by the electrode graphics in FIG. 3. Deployment of the electrodes causes the AED to power on. When the rescue protocol first calls for rhythm analysis and possible shock delivery, the rescuer stands clear of the victim as the AED receives and analyzes the victim's ECG and automatically delivers one or more shocks when a shock is advised. After shock delivery the AED enters a CPR interval during which CPR is administered. During the CPR interval, or during an initial CPR interval when called for by the rescue protocol, the AED housing is placed on the victim's sternum adjacent to the electrodes attached to the victim's torso. CPR chest compressions are then administered by pressing against the top of the AED on the victim's chest, guided by the audible prompts and beeps and by the blinking LED 34. After the CPR interval, the AED resumes rhythm analysis in accordance with the rescue protocol.

Figure 4:
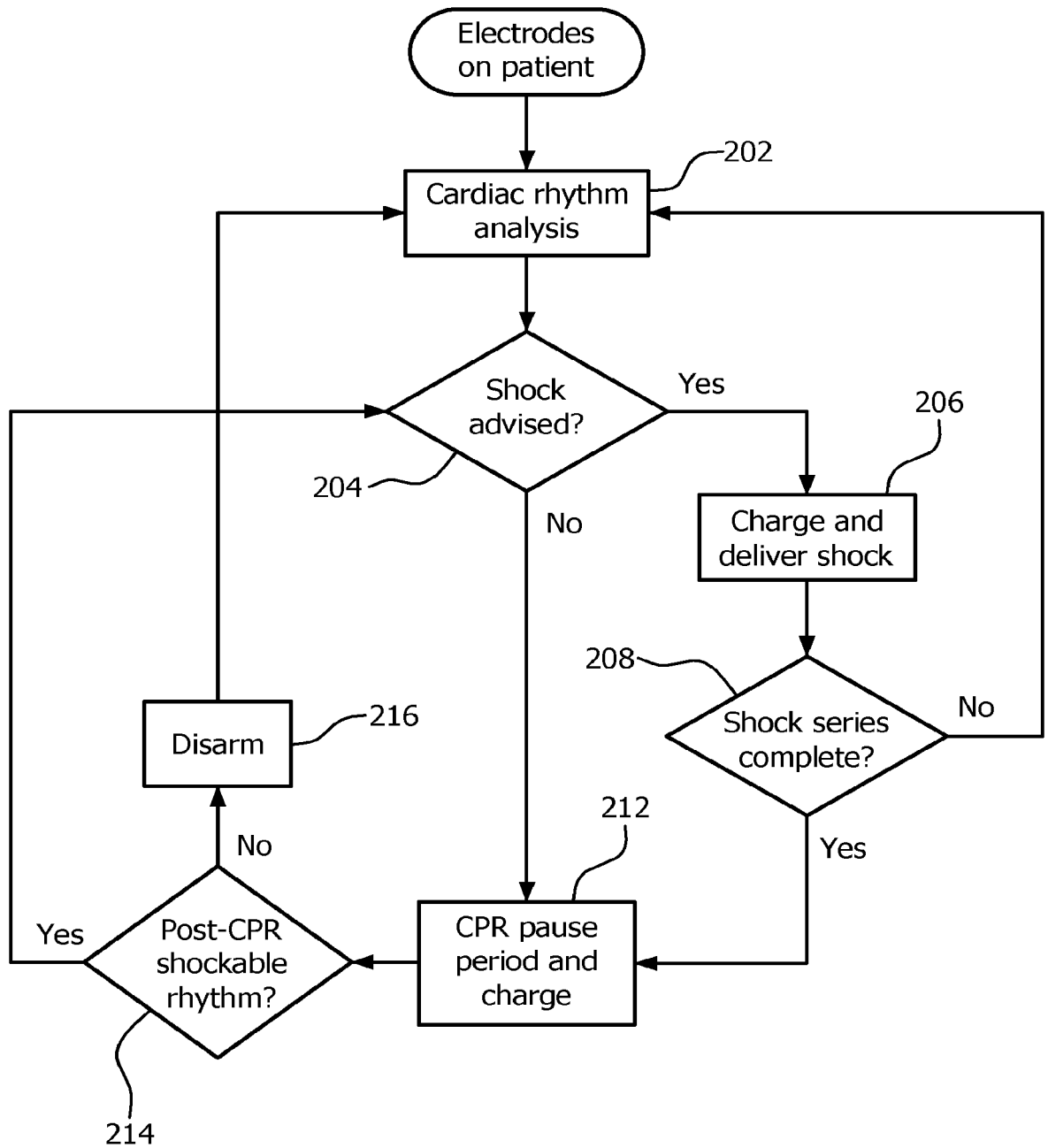
FIG. 4 is a flow diagram of a defibrillator operating protocol incorporating a CPR pause mode of operation.

An AED with a mode of operation (protocol) including a "CPR pause" period is illustrated in FIG. 4. Since studies have shown that early CPR can play a critical role in patient recovery, this mode is becoming increasingly popular as an AED resuscitation protocol. Following attachment of the electrodes to the patient, the AED analyzes the patient's cardiac rhythm at step 202. During the analysis, the AED is precharged in preparation for possible delivery of electrotherapy. Based on the rhythm analysis, a determination is made at step 204 whether to advise the delivery of electrotherapy. If the analysis reveals a "shockable rhythm" in the patient's cardiac rhythm, delivery of electrotherapy is advised and at step 206 the AED is fully charged and a defibrillation pulse is automatically delivered by the AED to resuscitate the patient. This sequence can be repeated two additional times if the patient has not been resuscitated and a shockable rhythm is detected, resulting in a total delivery of three shocks. Another electrotherapy protocol is a "single shock" protocol as described in US pat. pub. no. US2008/0312708 (Snyder). At the end of the shock sequence 208 or when a shock is not advised at 204, the AED enters a CPR pause period at 212. As CPR is performed by the rescuer, audible and/or visual prompts are given by the AED to instruct the rescuer on the proper administration of CPR. A synchronous (metronome) tone may be produced by the AED to guide the rescuer in the proper rate of chest compressions. Typically, the CPR pause period is on the order of one minute or more. Toward the end of the CPR pause period the AED is precharged in preparation for a possible post-CPR shock delivery. At the conclusion of the CPR pause period the ECG is again analyzed for a shockable rhythm at 214 and if none is detected, the precharge is disarmed at 216 and the process returns to the initial rhythm analysis step 202. If a shockable rhythm is detected in this step, the protocol continues to advise a shock at 204 and the AED delivers the shock at 206.

An AED kit of the present invention is shown in FIG. 5. As seen from the above, the kit is very simple, including an AED 100, a charger or docking station 52, 68, 69, and instructions. The kit is generally sent to an owner or lessee in packaging 70.

When the kit is received the charger or docking station is plugged in and the AED connected as illustrated in FIG. 7 for a tabletop docking station 68. A wall mount docking station 69 is also available for facilities like office buildings where fixed and visible AED locations are desired, as shown in FIG. 6. The docking station 69 is seen to be connected to an a.c. outlet on the wall below the docking station, and may also be connected to a telephone or other communication line. When the docking station is installed as illustrated, it begins its periodic transmission of self-test results or unsuccessful self-test messages as indicated by the radio waves next to the AED 100.

Figure 9:
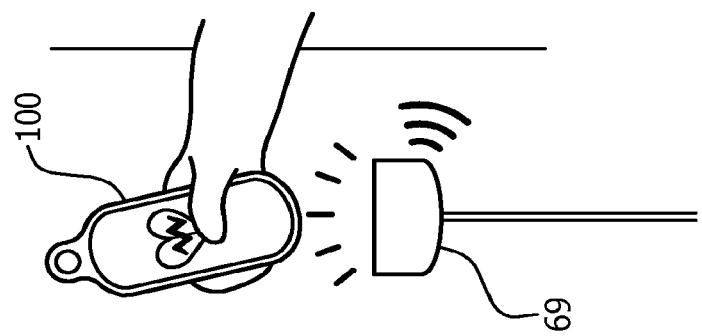
FIG. 9 illustrates removal of and AED from its wall-mounted charger.
Figure 8:
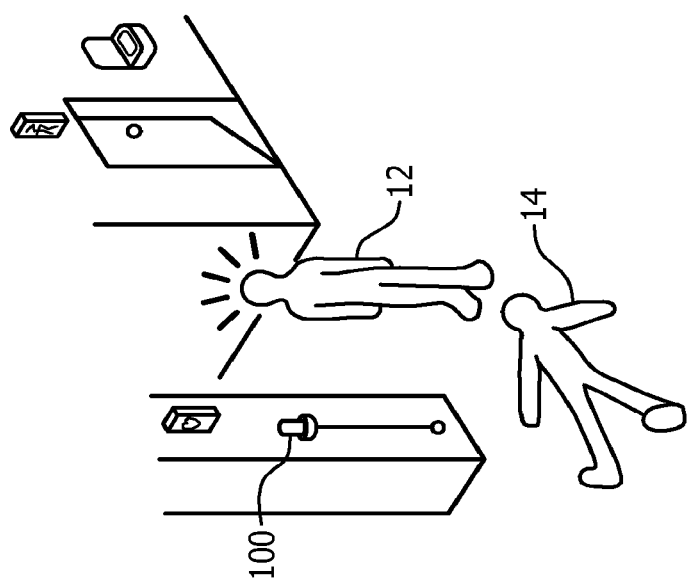
FIG. 8 depicts a rescuer at the site of an SCA victim.

A typical rescue of a patient stricken with SCA is illustrated in FIGS. 8-13. FIG. 8 illustrates a prone, unconscious patient 14 and a rescuer 12 near the wall-mounted AED 100. The rescuer removes the AED from the wall mounted docking station 69 as shown in FIG. 9. In this implementation a communication unit is located in the docking station 69 and is triggered by the removal of the AED 100 from the docking station to place a call to an emergency response service (such as 9-1-1 in the United States). The communication unit then plays a pre-recorded message, requesting medical assistance be sent to the location of the AED as described in the aforementioned Morgan '841 patent publication.

Figure 12:
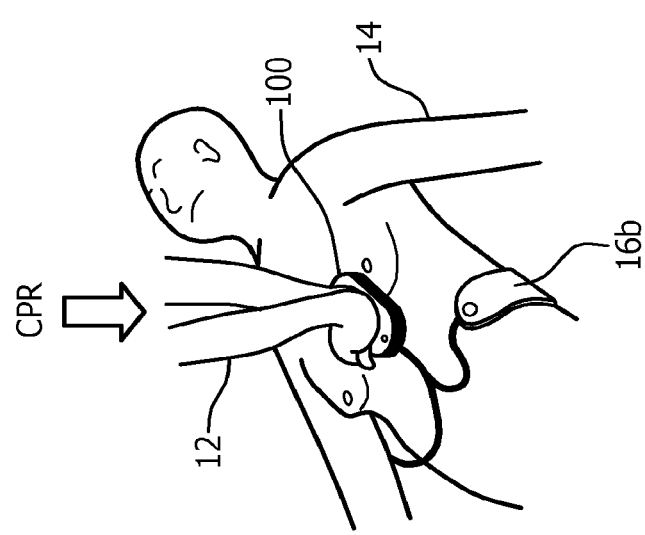
FIG. 12 illustrates the application of CPR chest compressions by means of an AED of the present invention.

With the AED removed from its docking station, the rescuer hooks a finger through the prominent loop 76 at the top of a tear strip 74 that is wrapped around the AED 100 as shown in FIG. 10a. The tear strip holds a polymeric sheet cover 80 over and around the top of the AED which contains the electrodes 16a, 16b. The cover 80 protects the electrodes prior to use and keeps them packaged with the AED. The tear strip 74 contains a perforation 78 which enables the tear strip to be easily torn and removed when the loop 76 is pulled as indicated by the arrow in FIG. 10a. In this example the tear strip is conductive at the location of the perforation 78 and electrically coupled to the deployment sensor 26 of the AED 100. While the perforation is intact it completes a circuit and the AED is turned off. When the perforation 78 is broken as shown in FIG. 10b, the opening of the electrical continuity provided by the unbroken tear strip is sensed by the deployment sensor which causes the AED to turn on. The tear strip 74 is discarded and the cover 80 removed as shown in FIG. 10c, revealing the electrodes 16a, 16b located on top of the AED 100. The electrodes are pre-connected to the AED 100 as shown in FIG. 10d. The electrodes 16a, 16b are now peeled away from their release liner and applied to the torso of the patient 14 as shown in FIG. 11. When CPR chest compressions are to be applied, the AED 100 is placed on the patient's sternum as indicated by the icon on top of the AED as shown in FIG. 10d. The rescuer 12 administers chest compressions by pressing against the AED 100 as shown in FIG. 12. In this implementation the AED 100 has two lighted arrows on the top of the housing as shown at 90 in FIG. 10d. The rescuer is guided in the performance of CPR by these two illuminated arrows. When a downward chest compression is to be applied to the patient's chest, the "down" arrow blinks and a tone is emitted by the speaker 38. When the compression is to be released the "up" arrow blinks. As long as compressions are being administered properly these arrows blink green in succession. If a deeper or shallower compression is to be applied, or a fuller compression release is needed, the appropriate arrow blinks yellow, accompanied by a verbal instruction from the speaker 38.

Figure 13:
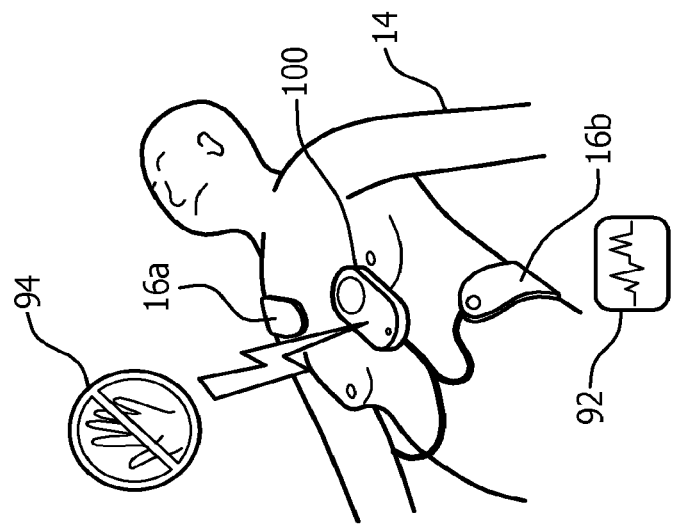
FIG. 13 illustrates an AED of the present invention when analyzing a patient's ECG and delivering a shock.

During an analysis period or shock delivery, a verbal prompt 94 is delivered by the speaker 38, warning the rescuer not to touch the patient as indicated in FIG. 13. The AED then receives ECG signals of the patient through the electrodes as indicated at 92. If the analysis of the heart rhythm indicates that a shock is advised, the AED 100 again warns the rescuer not to touch the patient because a shock is going to be delivered. A shock is delivered and the AED then either resumes ECG monitoring and analysis or enters a CPR period as called for by the rescue protocol being used.

When a large facility is outfitted with AEDs, such as an airport or large office building, the AEDs are generally installed on racks or in cases around the facility. A maintenance procedure must then be put in place to regularly inspect all AEDs to see that their LEDs are blinking green so that they are ready for use at all times. Such a maintenance routine is time consuming and is avoided with an AED of the present invention, because the AED will communicate any problems discovered by self-testing to a central maintenance facility. A local onsite maintenance person can then be contacted by the central facility and told to repair or return the AED which sent the diagnostic message to the remote facility. There is no longer any need for the onsite person to set up and carry out an inspection schedule for the AEDs since the AEDs will themselves report their problems to a central facility.

In accordance with another aspect of the present invention, this ability of an AED to report its self-diagnosis to a central location enables a replacement use model, where diagnostic problems are largely avoided by using an AED for only a single rescue. The AED is also periodically swapped out and replaced by another AED after a predetermined interval such as one year. In addition, a user may rent an AED and keep it at hand only during those times that its possible use may be expected, such as when a friend or relative at risk for cardiac arrest is living in the household. For example, a potential victim or rescuer may lease the AED for an indeterminate period of time, returning it when it is no longer needed. When the AED is brought to the location where it is to be kept ready for use, a pull tab is removed from the battery compartment to cause the AED to power up and conduct a self-test, as described in U.S. Pat. No. 8,086,306 (Katzman et al.) The AED is connected to its charger or docking station where the AED remains fully charged and ready for use until needed. There is no need to periodically inspect the AED since the AED will communicate any maintenance problems discovered during self-test to a central maintenance facility which will take care of all maintenance problems. If a problem is discovered, the facility will call or contact the custodian or lessee and arrange to send a replacement AED or deliver and set up another AED. All that the lessee has to do is pay a small monthly lease fee until the AED is returned to the lessor. If the AED is deployed for a rescue, the AED is returned after the rescue and replaced with another AED. The returned AED is refurbished and readied for use by another lessee. If the AED remains undeployed for a given period of time, such as one year, the AED is replaced by another AED and the original AED returned to the lessor. The custodian may keep the charger or docking station and use it with the newly supplied AED. The returned AED is refurbished, its battery and electrodes replaced with fresh ones, and the returned AED is then ready for delivery to another lessee or to replace one that has had its one-year time of service expire. This use model means that private individuals can have an AED in the home only when they want to have one and can return it at any time. They never have to worry about maintenance of a stored AED as the AED will report its own problems to a facility that will respond to them. These private individuals will always be assured that the AED is in fully operational condition as the AED is replaced with a fresh one every year. And if the AED is ever used, it is then immediately replaced with a fresh one. When the AED is deployed for a rescue, there is virtually nothing to do except apply the electrodes to the chest of the patient and stand back while the AED automatically diagnoses and resuscitates the victim. If CPR is called for, no additional equipment is needed and the AED guides the rescuer in the proper administration of CPR using the AED.

Before the AED is returned undeployed at the end of its year of storage, the AED can be used by a potential rescuer for training. The outline of the head and torso of a victim is printed on the inside of the packing materials for the AED or on the back of the instruction sheet 72. These materials can be laid flat and used by the rescuer/trainee to practice AED deployment. The electrodes are deployed and the rescuer/trainee practices applying them to the proper torso locations of the printed mannequin. Through the use of conductive ink to print the mannequin, the circuit 20 will see a given impedance presented by the conductive ink of the mannequin when the electrodes are correctly placed on the mannequin and the AED will simulate the delivery of a shock. The speaker 38 then announces to the rescuer/trainee that the the training was successful. The AED is then packaged for shipment and returned to the refurbishment facility.

What is claimed is:

1. An automated external defibrillator (AED) arranged for no more than a single use for a single rescue at a customer location, and for a predetermined period of time, the AED comprising:
   a battery, wherein the battery has a capacity to support delivery of only a limited number of shocks for the single use;
   a connector for coupling the AED to an external power source for continually charging the battery from the power source such that the AED is stored and maintained ready for use to resuscitate a subject;
   a controller configured to execute self-testing routines periodically to test a plurality of functions and capabilities of the AED in order to determine a readiness for use of the AED;

a set of electrodes that are attached to the AED and in electrical communication with the controller; and a communication unit in communication with the controller, the communication unit being configured to electronically transmit, based on a failed readiness for use determination, a service message for returning the AED to a supplier in response to either (i) an end of the predetermined period of time, or (ii) prior to an expiration of the predetermined period of time, a single usage of the AED for a rescue, as indicated by a sensed deployment of the set of electrodes.

2. The AED of claim 1, further comprising:

an electrically conductive tear strip; and a deployment sensor in communication with the tear strip and disposed to sense an opening of electrical continuity provided by the tear strip to indicate that sensed deployment.

3. The AED of claim 1, further wherein the electronically transmitting the service message for returning the AED to the supplier is further in response to, prior to expiration of the predetermined period of time, a determination by the controller that the AED is not ready for use.

4. The AED of claim 3, wherein the determination further comprises determining at least one of a condition of a battery of the AED, a condition of electrodes of the AED, or a functioning of circuitry of the AED.

5. The AED of claim 4, wherein the AED further comprises one or more of an audio or visual device for issuing a customer alert configured to alert the customer to a determination that the AED is not ready for use.

* * * * *